US010914578B2

(12) United States Patent
Cattin et al.

(10) Patent No.: US 10,914,578 B2
(45) Date of Patent: Feb. 9, 2021

(54) APPARATUS AND METHOD FOR DETERMINING THE ORIENTATION AND POSITION OF TWO RIGID BODIES

(71) Applicant: UNIVERSITÄT BASEL, Basel (CH)

(72) Inventors: Philippe C. Cattin, Windisch (CH); Lorenzo Iafolla, Monte Porzio Catone (IT); Lilian Witthauer, Basel (CH)

(73) Assignee: UNIVERSITÄT BASEL, Basel (CH)

( * ) Notice: Subject to any disclaimer, the term of this patent is extended or adjusted under 35 U.S.C. 154(b) by 0 days.

(21) Appl. No.: 16/470,497

(22) PCT Filed: Dec. 15, 2017

(86) PCT No.: PCT/EP2017/083171
§ 371 (c)(1),
(2) Date: Jun. 17, 2019

(87) PCT Pub. No.: WO2018/109218
PCT Pub. Date: Jun. 21, 2018

(65) Prior Publication Data
US 2020/0109940 A1    Apr. 9, 2020

(30) Foreign Application Priority Data
Dec. 16, 2016 (EP) ..................... 16204596

(51) Int. Cl.
*G01B 11/26* (2006.01)
*A61B 1/005* (2006.01)
(Continued)

(52) U.S. Cl.
CPC ............ *G01B 11/26* (2013.01); *A61B 1/0055* (2013.01); *G01D 5/28* (2013.01); *G02B 23/2476* (2013.01); *A61B 2562/185* (2013.01)

(58) Field of Classification Search
CPC . G01B 11/26; A61B 1/0055; A61B 2562/185; G01D 5/28; G02B 23/2476
See application file for complete search history.

(56) References Cited

U.S. PATENT DOCUMENTS 5,461,472 A    10/1995  Harvey et al.
8,184,277 B2   5/2012   Bove et al.
(Continued)

FOREIGN PATENT DOCUMENTS

DE    20 2012 004886 U1    7/2012
DE    20 2014 007764 U1    10/2014
WO    2012/007561 A2       1/2012

OTHER PUBLICATIONS

International Search Report dated Feb. 23, 2018 in corresponding International Patent Application No. PCT/EP2017/083171.

*Primary Examiner* — Jamil Ahmed
(74) *Attorney, Agent, or Firm* — Medler Ferro Woodhouse & Mills PLLC

(57) ABSTRACT

An apparatus for determining a position and orientation of first and second rigid bodies in relation to each other. The apparatus includes a light source mounted to the first rigid body, an image sensor mounted to either the first or second rigid body and positioned in a field of light, a shadow mask mounted to either the first or second rigid body and arranged in the field of light, and a computation unit configured to calculate at least one angle by evaluating a shadow image which passes the shadow mask and is detected by the image sensor. The apparatus may include a mechanical constraint mounted to the first and second rigid bodies that defines a fixed distance between the first and second rigid bodies, is stationary in relation to one of the first or second rigid body, and is variably inclinable in relation to the other.

15 Claims, 4 Drawing Sheets

(51) Int. Cl.
*G01D 5/28* (2006.01)
*G02B 23/24* (2006.01)

(56) References Cited

U.S. PATENT DOCUMENTS

| | | | |
|---|---|---|---|
| 2015/0359418 A1* | 12/2015 | Feussner | A61B 5/055 600/411 |
| 2016/0153774 A1* | 6/2016 | Kodaira | G01M 11/08 356/364 |
| 2018/0185045 A1* | 7/2018 | Ohki | G02B 23/24 |

\* cited by examiner

APPARATUS AND METHOD FOR DETERMINING THE ORIENTATION AND POSITION OF TWO RIGID BODIES

TECHNICAL FIELD

The present invention relates to an apparatus and method for determining the orientation and position of at least two rigid bodies in relation to each other and more particularly to an endoscopic device including such an apparatus.

Such an apparatus comprising an at least essentially punctual light source mounted stationary in relation to the first rigid body; an image sensor mounted stationary in relation to either the first rigid body or the second rigid body and positioned in a field of light propagated by the light source; a shadow mask mounted stationary in relation to either the first rigid body or the second rigid body and arranged in the field of light propagated from the light source between the light source and the image sensor;

and a computation unit configured to calculate at least one angle by evaluating a shadow image generated by light propagated by the light source which passes the shadow mask and which is detected by the image sensor, can be used for efficiently measuring the position and orientation of the rigid bodies in relation to each other.

BACKGROUND ART

In order to gain information about the position and orientation of bodies in relation to each other, positioning devices are frequently used across several technical domains in the art. There are techniques used which are based on many type of sensors such as resistive strain, piezoelectric, piezoresistive, capacitive, inductive or similar sensors and methods. For example, such devices can involve optical devices such as laser interferometers, measurement of the time of flight of a laser pulse, cameras, stereo-cameras and the like.

Referred to rigid bodies, usually six-dimensional (6D) positioning is necessary since position and orientation are defined with six degrees of freedom such as x-, y-, z-, pitch-, roll- and yaw-position/orientation. In some applications this type of measurement is done with 6D cameras which essentially is a stereo camera. Thereby, on the tracked body usually three or more light sources are applied on some determined positions in order to allow a precise detection of the position and orientation.

For example, the document WO 2012/007561 A1 discloses a system that computes the azimuth and the elevation of a light source with respect to a sensor with high precision. The document U.S. Pat. No. 8,184,277 B2 describes an optical device for determining an angular position of a rotating element. The document U.S. Pat. No. 5,461,472 A describes a technique for determining the degree of parallelism of two surfaces.

Even though there are plural devices known in the art which allow for precise measurement of position and orientation of two bodies in relation to each other such devices usually are quite complicated and, if a comparably high precision is required, cost expensive. Furthermore, such devices usually are comparably bulky such that they are difficult to be used in applications where comparably little space is available. For example, in minimal invasive surgical applications there usually is only little space available. Thus, for being used in such conditions conventional devices usually are not appropriate.

Therefore, there is a need for a device and a method for determining the orientation and position of two bodies in relation to each other which requires comparably little space and is comparably precise and affordable.

DISCLOSURE OF THE INVENTION

According to the invention this need is settled by an apparatus as it is defined by the features of independent claim 1, by a method as it is defined by the features of independent claim 14 and an endoscopic device as it is defined by the features of independent claim 15. Preferred embodiments are subject of the dependent claims.

In particular, the invention deals with an apparatus for determining a position and orientation of a first rigid body and a second rigid body in relation to each other. The apparatus comprises an at least essentially punctual light source mounted stationary in relation to the first rigid body; an image sensor mounted stationary in relation to either the first rigid body or the second rigid body and positioned in a field of light propagated by the light source; a shadow mask mounted stationary in relation to either the first rigid body or the second rigid body and arranged in the field of light propagated from the light source between the light source and the image sensor; and a computation unit configured to calculate at least one angle, preferably two angles, by evaluating a shadow image generated by light propagated from the light source which passes the shadow mask and which is detected by the image sensor.

Further, the apparatus comprises a mechanical constraint mounted to a first connection spot of the first rigid body and to a second connection spot of the second rigid body. The mechanical constraint defines a fixed or predefined distance between the first connection spot of the first rigid body and the second connection spot of the second rigid body. It is stationary in relation to one of the first rigid body or the second rigid body. Further, it is variably inclinable in relation to the other one of the first rigid body and the second rigid body.

The term "light propagated by the light source" can relate to light emitted by the light source and having a direction into which it is forwarded. The propagated light can comprise light directly emitted from the light source as well as light originating from the light source which is reflected, e.g., by a mirror.

The image sensor can be a device adapted to sense light and particularly to recognize a structure or shape of the light. It can have a light sensing surface wherein various sections of the light sensing surface do individually sense the light. For example the image sensor can comprise a plurality or an array of light sensors arranged such that they together form the light sensing surface.

The term "stationary" as used in connection with two elements of the apparatus in relation to each other can relate to an essentially or completely fixed spatial position of the two elements to each other. There can still be spatial flexibility or movability in relation to other elements but the involved elements are quasi immovable towards each other or quasi inter-immovable. Advantageously, for being stationary in relation to each other the two elements are fixedly mounted on each other. Such fixed mounting can be directly or indirectly via another element. For example, the image sensor can be mounted stationary in relation to the first rigid body by being glued, bonded or screwed to the rigid body. Or, e.g., the light source can be mounted stationary to the first rigid body by being fixed in a holder which is connected to the first rigid body.

The term "variably inclinable" in connection with the mechanical constraint and the other one of the first rigid body or the second rigid body relates to the mechanical constraint being arrangeable in various inclined orientations towards the other one of the first rigid body or the second rigid body. This can be embodied by arranging these elements such that the mechanical constraint and the other one of the first rigid body or the second rigid body can be turned, rotated or tilted towards each other. Thereby, the mechanical constraint can be more or less inclined in relation to the other one of the first rigid body or the second rigid body.

The mechanical constraint can be a rigid structure such as, e.g., a post, a bar, a rail or the like. It can be made of a material which is robust enough for being rigid in the intended application of the apparatus. As the need may be differing such materials can be used.

The shadow mask can be an object which prevents all or specific frequencies of light to pass. It can particularly be made of a light absorptive or opaque material. Furthermore, the shadow mask advantageously is shaped such that the orientation and position of the body it is stationary mounted to can be determined with respect to the other body. For example it can be shaped or arranged to allow portions of the light to pass and other portions not. By being positioned in the field of light propagated by the light source between the light source and the image sensor the shadow mask generates a shadow image on the sensor. Thereby, the image is depending on the position of the first and second bodies to each other. In particular, in any position and orientation the shadow mask generates a unique shadow image on the image sensor. Like this, by evaluating the shadow image generated on the image sensor, it can be concluded how the two bodies are arranged to each other.

In accordance with the invention the degrees of freedom of the relative movements of the two rigid bodies are movable in relation to each other is reduced by the mechanical constraint. This allows for providing an exactly defined number of degrees of freedom only, such as one or two angles like a pitch angle and/or a yaw angle. The distance of the two rigid bodies to each other is fixed or predefined by the mechanical constraint such that only a tilting of one body in relation to the other body about the two axis is possible. This allows in a comparably compact arrangement to exactly and efficiently determine the position as well as the orientation of the two rigid bodies to each other.

Further, the apparatus according to the invention can be used in a cascaded arrangement having a plurality of first and second rigid bodies or plural apparatuses. Like this, a chain like device can be formed in which position and orientation of each chain link can be exactly determined such that the course of the chain can precisely be determined.

The present invention proposes to measure at least one or two angles such as pitch and yaw that define the orientation and position of one rigid body referred to another. In order to use this technique the variations over the others degrees of freedom are measured or bounded with the mechanical constraint. The components of the apparatus can be arranged in a way that a variation of the at least one angles determines a variation of the shadow image or shadow projected by the shadow mask on the image sensor. The shadow mask and the system are configured in a way that the shadow image can identify, with a one-to-one correspondence, the relative orientation of the two bodies.

In a preferred embodiment the image sensor is mounted stationary in relation to the second rigid body. This allows for providing the light from the first body and detecting it at the second body. Since the shadow mask is positioned in between the first and second bodies the shadow image is generated on or near the second body. Like this, an efficient arrangement of the apparatus is possible in which a comparably small number of parts is necessary.

In another preferred embodiment, a mirror is mounted stationary in relation to the second rigid body and the image sensor is mounted stationary in relation to the first rigid body. In such an arrangement, the light can be emitted at or near the first body being reflected at or near the second body and provided back to the first body where the image sensor is situated. This allows to enhance the propagation of the light or the travel distance of the light from the light source to the image detector even in comparably compact arrangements. Like this, particularly when the shadow mask is positioned between the light source and the image sensor, the shadow image generated on the image sensor changes more efficiently such that a precise determination of the position and orientation is possible.

Thereby, the mirror can have a flat but preferably has a curved surface. Such a curved surface allows for amplifying the changes of the shadow image being generated on the image sensor. This allows for increasing the accuracy in terms of the position and orientation.

In a preferred embodiment, the curved or otherwise three-dimensionally shaped or non-flat surface of the mirror comprises plural sections arranged to reflect light in different quality such as in different colors or the like. For example, the sections of the surface of the mirror can be equipped with different filters allowing the adapt or specify the quality or color of the reflected light. In particular, these sections can be embodied to reflect the same, e.g. white, light in different qualities or colors towards the image sensor. By such an arrangement, in particular since the sections of the surface of the mirror are spaced apart from each other, the range of inclination of the first and second bodies relative to each other detectable by the image sensor can be increased. Thereby, the image sensor preferably is arranged to differentiate the color of detected light. The image sensor or the computation unit can then evaluate from which section of the mirror the detected light is reflected since each section generates a different shadows on the image sensor. In particular, the color sensitive image sensor allows identifying from which sector of the surface of the mirror originates. If now, e.g., the first and second rigid bodies are inclined to each other to an extent such that only the light of one lateral section of the surface of the mirror is detected, it is still possible to evaluate from which one of the sectors the detected light originates such that the orientation and position of the first and second rigid bodies relative to each other can still be exactly determined.

Preferably, the shadow mask is mounted stationary in relation to the first rigid body. This allows for a comparably simple and efficient set up for generating the shadow image.

Preferably, the mechanical constraint is adapted to hold the first rigid body and the second rigid body in a predefined relative position to each other such that the shadow image has a one-to-one correspondence=f(shadow image, relative position) with at least one angle. Or in other words, such that the shadow image is a function of the at least one angle and vice versa. Thereby the relative position preferably is fixed by the mechanical constraint such that exclusively the at least one angle is changeable. Also, the computation unit preferably is configured to calculate the one-to-one correspondence=f(shadow image, relative position) by interpolating input data provided by the image sensor in a calibration step.

Preferably, the image sensor and/or the computation unit is configured to differentiate light detected by the image sensor into light propagated by the light source and other light. Thereby, the image sensor and/or the computation unit preferably is adapted to filter the other light from the light detected by the image sensor. Such a arrangement allows for reducing perturbing or disruptive effects induced by other light present in the environment of the apparatus. Like this, the accuracy of the measured position and orientation can be enhanced.

Preferably, the shadow mask comprises a pattern having distinctive elements. Such a patterned shadow mask can allow for making evaluation of the shadow image more efficient and accurate. In particular, such distinctive elements may be exactly identified which allows to precisely determine the shadow image in the light by the image sensor.

Preferably, the apparatus further comprises a further second rigid body; a further at least essentially punctual light source mounted stationary in relation to the first rigid body; a further image sensor mounted stationary in relation to either the first rigid body or the further second rigid body and positioned in a field of light propagated by the further light source; a further shadow mask mounted stationary in relation to either the first rigid body or the further second rigid body and arranged in the field of light propagated from the further light source between the further light source and the further image sensor; and a further mechanical constraint mounted to a further first connection spot of the first rigid body and to a further second connection spot of the further second rigid body, wherein the mechanical constraint defines a fixed distance between the further first connection spot of the first rigid body and the further second connection spot of the further second rigid body, is stationary in relation to one of the first rigid body or the further second rigid body, and is variably inclinable in relation to the other one of the first rigid body and the further second rigid body; and wherein the computation unit is configured to calculate at least one further angle by evaluating a shadow image generated by light propagated from the further light source which passes the further shadow mask and which is detected by the further image sensor.

Such an apparatus allows for providing a multi branched arrangement wherein the first body can be the common first body for more than one second bodies. This allows for efficiently embodying the apparatus in accordance with an intended application thereof.

In a preferred embodiment, the apparatus comprises at least one at least essentially punctual further light source mounted stationary in relation to the first rigid body and offset from the light source, wherein the light source and the at least one further light source are arranged to propagate light of different colors. By such an arrangement of plural light sources spaced from each other and providing light of different colors the range of inclination of the first and second bodies relative to each other detectable by the image sensor can be increased. Thereby, the image sensor preferably is arranged to differentiate the color of detected light. Thus, the image sensor or the computation unit can evaluate from which light source of the light source and the at least one further light source the detected light originates. For example, the apparatus can be equipped with a red light emitting diode (LED), a green LED and a blue LED being spaced from each other. The color sensitive image sensor allows identifying from which one of the light sources which portion of the detected light originates. In particular, in such an arrangement plural different shadows can be generated on the image sensor. If now the first and second rigid bodies are inclined to each other to an extent such that only the light of one lateral light source reaches the image sensor, it is still possible to evaluate from which one of the light sources the detected light originates such that the orientation and position of the first and second rigid bodies can still be exactly determined. Such range of inclination would not be detectable with a single light source or with plural light sources propagating light of one single color. The special distribution of the light source and the at least one further light source preferably is adapted to the geometric arrangement of the first and second bodies as well as the image sensor.

In another preferred embodiment, the apparatus comprises a shield structure protecting the image sensor from light disturbances. The term "light disturbances" used in this context can relate to anything affecting the generation of the shadow image on the image sensor. For example, such light disturbances can be light not originating from the light source or the at least one further light source but, e.g., originating from an external light source or being ambient light. Such light disturbances may impair the quality or accuracy of the shadow image. The shield structure can particularly be arranged to cover or protect the field of light propagation in the apparatus. Like this, the light detected by the image sensor can be protected from external light sources or other light disturbances. This allows for increasing or assuring quality of light detection by the image sensor and evaluation by the computation unit.

Another aspect of the invention relates to a method of determining a position and orientation of a first rigid body and a second rigid body in relation to each other. The method comprises the steps of: mounting an at least essentially punctual light source stationary in relation to a first rigid body of the two rigid bodies; positioning an image sensor in a field of light propagated from the light source; mounting the image sensor stationary in relation to either the first rigid body or a second rigid body of the two rigid bodies; mounting a shadow mask stationary in relation to either the first rigid body or the second rigid body; arranging the shadow mask in the field of light propagated from the light source between the light source and the image sensor; calculating at least one angle by evaluating a shadow image generated by light propagated from the light source which passes the shadow mask and detected by the image sensor; mounting a mechanical constraint to a first connection spot of the first rigid body and to a second connection spot of the second rigid body, wherein the mechanical constraint defines a fixed or predefined distance between the first connection spot of the first rigid body and the second connection spot of the second rigid body, is stationary in relation to one of the first rigid body or the second rigid body, and is variably inclinable in relation to the other one of the first rigid body and the second rigid body.

Such a method allows for efficiently implementing the effects and benefits described above in connection with the apparatus according to the invention and its preferred embodiments.

Another further aspect of the present invention relates to an endoscopic device having a longitudinal body adapted to be provided into a lumen of a human or animal body and an intervention member arranged at a distal longitudinal end region of the longitudinal body. The longitudinal body of the endoscopic device comprises a series of apparatuses according as described above.

In this context, the term "distal longitudinal end region" can relate to a section at or near and end of the longitudinal body which is to be entered into the lumen. Such an endoscopic device allows for implementing the effects and benefits described above in connection with the apparatus according to the invention and its preferred embodiments. In a surgical and/or in a clinical environment such as, particularly for minimally invasive surgery, this can be highly advantageous since the position of the endoscope and particularly its intervention member in many case is crucial for the success of the therapeutic or surgical application. Thereby, the endoscope allows for precisely locating the intervention member inside the body without necessarily applying further cumbersome procedures such as imaging or the like.

The term "intervention member" can relate to any structure suitable for an intended endoscopic application. For example, the intervention member can be a camera for monitoring the situation in the lumen of the body. Or it can be one or plural sensors such as a pressure sensor, a thermometer or the like. Also it can be a unit to be positioned inside the lumen such as a stent or the like. Preferably, the intervention member is a laser beam emitter adapted to provide a laser beam for ablating human or animal soft or hard tissue. Such a laser beam emitter allows for a gentle and precise cutting or removing of the tissue. And by means of the endoscope it can be precisely positioned and oriented for the intended ablation. The intervention member can also comprise any combination of sensors and/or tools as, e.g., mentioned.

Preferably, each two consecutive rigid bodies of the series of apparatuses are rotatable or tiltable orthogonal to each other. Such arrangement allows for an efficient implementation of the endoscope.

Another aspect of the present disclosure comprises a method of manufacturing an apparatus as described above. The manufacturing method comprises obtaining a first rigid body, a second rigid body, an at least essentially punctual light source, an image sensor, a shadow mask, a mechanical constraint and a computation unit. It further comprises the steps of: mounting the light source stationary in relation to the first rigid body; mounting the image sensor stationary in relation to either the first rigid body or the second rigid body; positioning the image sensor in a field of light propagated by the light source; mounting the shadow mask stationary in relation to either the first rigid body or the second rigid body; arranging the shadow mask in the field of light propagated from the light source between the light source and the image sensor; configuring the computation unit to calculate at least one angle, preferably two angles, by evaluating a shadow image generated by light propagated from the light source which passes the shadow mask and which is detected by the image sensor; mounting the mechanical constraint to a first connection spot of the first rigid body and to a second connection spot of the second rigid body such that it defines a fixed distance between the first connection spot of the first rigid body and the second connection spot of the second rigid body; arranging the mechanical constraint stationary in relation to one of the first rigid body and the second rigid body; and arranging the mechanical constraint variably inclinable in relation to the other one of the first rigid body and the second rigid body.

BRIEF DESCRIPTION OF THE DRAWINGS

The apparatus, the method and the endoscope according to the invention are described in more detail herein below by way of exemplary embodiments and with reference to the attached drawings, in which.

DESCRIPTION OF EMBODIMENTS

In the following description certain terms are used for reasons of convenience and are not intended to limit the invention. The terms "right", "left", "up", "down", "under" and "above" refer to directions in the figures. The terminology comprises the explicitly mentioned terms as well as their derivations and terms with a similar meaning. Also, spatially relative terms, such as "beneath", "below", "lower", "above", "upper", "proximal", "distal", and the like, may be used to describe one element's or feature's relationship to another element or feature as illustrated in the figures. These spatially relative terms are intended to encompass different positions and orientations of the devices in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. The devices may be otherwise oriented (rotated 90 degrees or at other orientations), and the spatially relative descriptors used herein interpreted accordingly. Likewise, descriptions of movement along and around various axes include various special device positions and orientations.

To avoid repetition in the figures and the descriptions of the various aspects and illustrative embodiments, it should be understood that many features are common to many aspects and embodiments. Omission of an aspect from a description or figure does not imply that the aspect is missing from embodiments that incorporate that aspect. Instead, the aspect may have been omitted for clarity and to avoid prolix description. In this context, the following applies to the rest of this description: If, in order to clarify the drawings, a figure contains reference signs which are not explained in the directly associated part of the description, then it is referred to previous or following description sections. Further, for reason of lucidity, if in a drawing not all features of a part are provided with reference signs it is referred to other drawings showing the same part. Like numbers in two or more figures represent the same or similar elements.

Figure 1:
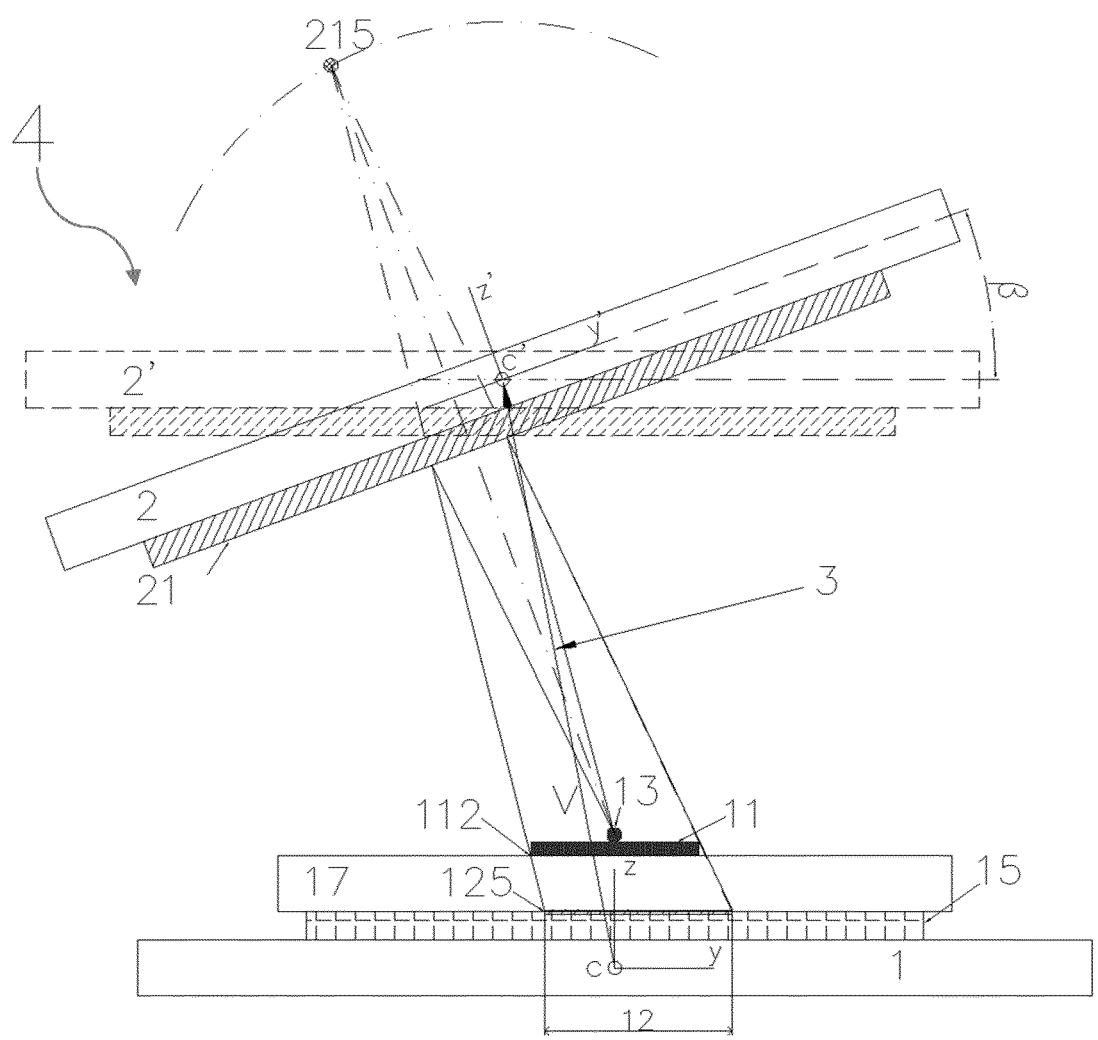
FIG. 1 shows a first embodiment of an apparatus according to the invention.

In FIG. 1 a first embodiment of an apparatus 4 according to the invention is shown. The apparatus 4 comprises a first rigid body 1, a second rigid body 2 and a mechanical constraint 3 connecting the first body 1 and the second body 2. The mechanical constraint 3 is fixedly mounted to the first rigid body 1 at a first connecting spot c thereof. Like this, the first body 1 and the mechanical constraint 3 are stationary in relation to each other. The mechanical constraint 3 further is tiltably mounted to the second rigid body 2 at a second connecting spot c' thereof. The mechanical constraint 3 has a fixed length defining a distance between the first connecting spot and the second connecting spot.

On a side facing the first rigid body 1 the second rigid body 2 is equipped with a mirror 21 which is fixedly mounted to the second body 2. On a side facing the second rigid body 2 the first rigid body 1 is equipped with an image sensor 15 which is fixedly mounted to the first body 1.

The apparatus 4 further comprises a shadow mask 11 and a punctual light source 13 which are assembled to one fixed unit. The shadow mask 11 and the light source 13 are mounted on top of the sensor 15 wherein a transparent spacer 17 is arranged between the shadow mask 11 and the sensor 15. Thereby, the shadow mask 11 and the light source 13 are mounted to the image sensor 15 and the first rigid body 1 stationary in relation to each other.

The position and the orientation of the two bodies 1, 2 are defined by the connecting spots c, c' and two triplets of axis, i.e. x-, y-, z-axis for the first rigid body 1 and x'-, y'-, z'-axis for the second rigid body 2. The position of the second connecting spot c' referred to the first connecting spot c is identified by a vector v.

The second rigid body 2 is in a preferred orientation when its three axis x', y' and z' are parallel to the axis x, y, z of the first rigid body 1. A rotation of the second rigid body 2 results it to be in a different orientation in relation to the first rigid body 1. The rotated second body 2' is tilted around the axis y' which is identified with the angle $\alpha$ while those around the axis x' with the angle $\beta$, being $\alpha=0$ and $\beta=0$ the values relate to the preferred orientation. The rotations around the axis z' are not considered, being them not influent for the preferred embodiment of the invention or prevented with some mechanical widget. Therefore, assuming xyz as the main reference frame, $\alpha$, $\beta$, and v will completely define the relative position and orientation of the rigid body 2 in relation to the first rigid body 1. The aim of the apparatus 4 particularly is to allow measuring $\alpha$ and $\beta$.

The apparatus 4 further comprises or is connected to a computation means which is configured in a way that given a certain relative position (v) of the two rigid bodies 1, 2, a shadow image 12 of the shadow mask 11 casted and detected by the image sensor 15 has a one-to-one correspondence $(\alpha,\beta)=f(12,v)$ with the angles $\alpha$ and $\beta$.

The mirror 21 is flat and attached to the rigid body 2 in a way that it reflects the light of the punctual light source 13 passing the shadow mask 11 and then on the image sensor 15 which detects the shadow or shadow image 12 of the shadow mask 11.

The rigid bodies 1, 2 are flat boards. The rigid body 1 includes a printed circuit board (PCB) that hosts at least the image sensor 15, the punctual light source 13 and the shadow mask 11. The rigid bodies 1, 2 have also some mechanical features to tie themselves with the mechanical constraint 3 at the connecting spots. For example, the two connecting spots c, c' are pins or holes on which the mechanical constraint 3 is screwed, threaded or inserted.

The rigid body 1 also has an electronic interface which carries the power supply and the data connection to the computing means or to a read-out device. The electronic interface can be a serial BUS such as USB or a wireless connection. The punctual light source 13 is as small as possible in order to have a sharp shadow on the image sensor, thus, it preferably is a LED (Light Emitting Diode). The punctual light source 13 is placed in the center of shadow mask 11 on the side facing the mirror 21.

The light from sources different from the punctual light source 13 is shielded in a way that it is not detected by the sensor 15. This allows to increase the signal to noise ratio. Alternatively or additionally, the punctual light source 13 can emit light at a particular wavelength in a way that it can be selected with a filter mounted on the image sensor 15. Again alternatively or additionally, a intensity of the punctual light source 13 is modulated in a way that, by means of Lock-In filter technique, all the other sources of light can be filtered.

The image sensor 15 is a digital sensor in a way that its output can be transmitted and processed with other digital devices and/or the computing means. For example, the image sensor 15 is a CMOS or a CCD sensor.

The shadow mask 11 contains parts that are transparent and parts that are opaque to light of the punctual light source 15. For example, it is printed using a standard lithography process. Furthermore, it contains a distinctive element whose shadow can be easily distinguished from the shadow of the other parts.

As an alternative to the transparent spacer 17, the gap between the image sensor 15 and the shadow mask 11 is empty and the shadow mask 11 is attached through a mechanical support to the first rigid body 1. Alternatively, a comparably thick shadow mask is attached directly to the image sensor 15 in a way that the principle of operation is still valid.

Rotating the second rigid body 2 around the axis x' (variation of $\beta$) or around the axis y' (variation of $\alpha$) as well as displacing it with respect to the first rigid body 1 (variation of v) will produce a different shadow image 12. If the shadow mask 11 has a distinctive element, given the relative position (v) of the second body 2 versus the first body 1, the one-to-one correspondence $(\alpha,\beta)=f(12,v)$ exists between the angles ($\alpha$ and $\beta$) and the shadow image 12. An equivalent virtual punctual light source 215 behind the second rigid body 2 can be considered instead of the punctual light source 13 as described in the geometrical optics theory and shown in FIG. 1. Thereby, it can be shown that the virtual punctual light source 215 lays on a curved surface 22 and its position is uniquely determined by the values of $\alpha$ and $\beta$. Given a point 112 of the distinctive element of the shadow mask 11 and the position of its shadow image 125 on the image sensor 15, it can be identified, tracing a straight line between these two points, only one point 215 on the curved surface 22. This point uniquely identifies the position of the virtual punctual light source 215 and, consequently, the values of $\alpha$ and $\beta$.

The shadow mask 11 comprises a repetitive pattern including distinctive elements. Indeed one single opening can be sufficient to perform the measurement, but, a pattern enables the system to perform several measurements and to improve the precision by averaging them. Nevertheless the repetitive feature of the pattern simplifies the definition of the one-to-one correspondence $(\alpha,\beta)=f(12,v)$.

In an alternative embodiment of the apparatus 4, the mirror 25 is curved (concave or convex) in order to change the resolution over the range ratio. Indeed the virtual punctual light source 215 will move on a different curved surface 22 producing bigger or smaller variations of the shadow image 125 on the image sensor 15 in function of $\alpha$ and $\beta$.

As discussed above, it can be fundamental to know the relative position v between the two rigid bodies 1, 2. Therefore, the rigid bodies 1, 2 are tied by the mechanical constraint 3 in a way that the relative position v does not change. In other words, the rigid bodies 1, 2 are tied to the same mechanical frame 3 in a way that the relative position v is fixed whilst one or both the angles $\alpha$ and $\beta$ can change.

In an alternative example, the rigid bodies 1, 2 are tied together with an elastic constraint and the variations of v are measured with strain gauges applied to the elastic constraint. In another example, the thermal expansion of the mechanical constraints is taken into account to estimate the variations of v. This can be done by measuring the temperature and calculating the expansion with known physical laws. In still another example, the relative position v is controlled with an actuator device changing the length of the mechanical constraints and then measured (e.g. with a linear encoder).

As mentioned, the evaluation of the one-to-one correspondence $(\alpha,\beta)=f(12,v)$ is fundamental to measure the angles $\alpha$ and $\beta$. To do so, the one to one correspondence $(\alpha,\beta)=f(12,v)$ can be calculated using the geometrical characteristics of the apparatus 4 and laws of optical physics. Alternatively, it is computed numerically with a software simulating the apparatus 4.

In the apparatus 4 the one-to-one correspondence $(\alpha,\beta)=f(12,v)$ is evaluated from an interpolation of a set of shadow images recorded for several values of $\alpha$, $\beta$ and, if variable, v, during a calibration procedure. The calibration values of $\alpha$, $\beta$, and v are to be chosen in order to cover uniformly their full range. Nevertheless, the accuracy of the interpolation depends on the density of the values of $\alpha$, $\beta$, and v used during the calibration procedure.

The computation means is an electronic device that can process the data from the image sensor and the measurements of v in order to evaluate the angles $\alpha$ and $\beta$. For instance it can be a general purpose microprocessor, an FPGA or a dedicated integrated circuit (IC). The computation means can be integrated in the same IC as the image sensor 15 or installed on the rigid body 1 and its outputs can be transmitted to a readout device through an electronic interface or a wireless connection. This solution has the advantage that the amount of data transmitted through the electronic interface or the wireless connection is severely reduced because only the two values of $\alpha$ and $\beta$ have to be transferred.

Alternatively, the computation means is installed outside the first rigid body 1 in a different support and the data output of the image sensor and the measurement of v (if it is not fixed) are transmitted through the electronic interface. The advantage of this approach is that the electronic system installed on the first rigid body 1 is simplified and the computation means has less requirements in terms of size, power consumption, etc.

Figure 2:
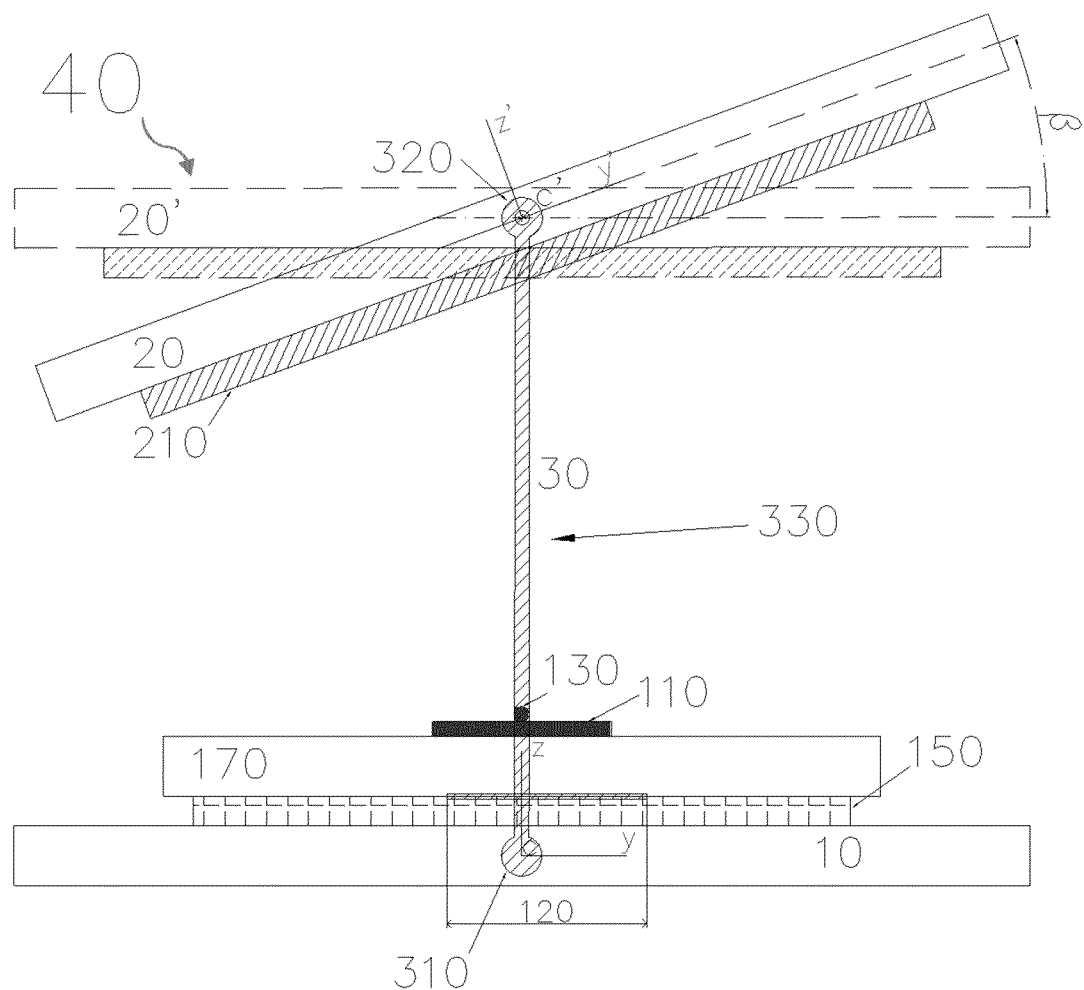
FIG. 2 shows a second embodiment of an apparatus according to the invention.

FIG. 2 shows a second embodiment of an apparatus 40 according to the invention. The apparatus 40 is similarly embodied and operated as the apparatus 4 of FIG. 1. In particular, where not mentioned otherwise, the apparatus 40 is identically embodied and/or operated as the apparatus 4.

The apparatus 40 comprises a first rigid body 10, a second rigid body 20 and a mechanical constraint 30 connecting the first body 10 and the second body 20. The mechanical constraint 30 comprises two bars 330, respective two first connectors 310 at first longitudinal ends of the bars 330 and respective two second connectors 320 at second longitudinal ends of the bars 330. Each first connector 310 is fixedly mounted to the first rigid body 10 at a first connecting spot thereof. Like this, the first body 10 and the mechanical constraint 30 are stationary in relation to each other. Each second connector 320 is tiltably mounted to the second rigid body 20 at a second connecting spot thereof. Thereby, the second body 20 is tiltable around the axis x' in relation to the mechanical constraint 30 and, thus, to the first body 10 by an angle $\alpha$. Thus, the one angle $\alpha$ can change only which provides one degree of freedom.

On a side facing the first rigid body 10 the second rigid body 20 is equipped with a mirror 210 which is fixedly mounted to the second body 20. On a side facing the second rigid body 20 the first rigid body is equipped with an image sensor 150 which is fixedly mounted to the first body 10.

The apparatus 40 further comprises a shadow mask 110 and punctual light source 130 which are assembled to one fixed unit. The shadow mask 110 and the light source 130 are mounted on top of the sensor 150 wherein a transparent spacer 170 is arranged between the shadow mask 110 and the sensor 150. Thereby, the shadow mask 110 and the light source 130 are mounted to the image sensor 150 and the first rigid body 10 stationary in relation to each other.

Figure 3:
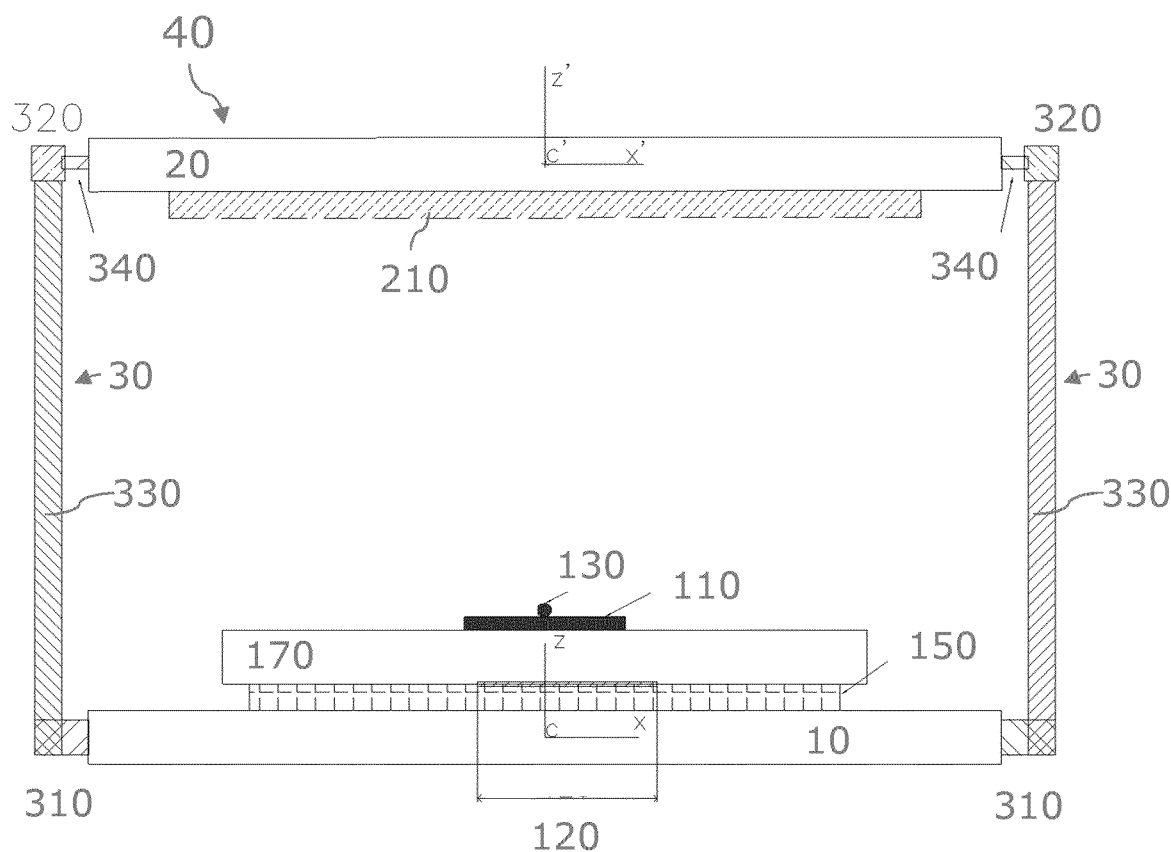
FIG. 3 shows the apparatus of FIG. 2 rotated by 90°.

In FIG. 3 the apparatus 40 is shown turned by 90°. Thereby, it is visible that the two bars 330 of the mechanical constraint 30 are embodied as two lateral arms. As explained above the two first connectors 310 are fixedly mounted to the first rigid body 10 at the first connecting spots thereof. The second connectors 320 are tiltably mounted to the second rigid body 20 at the second connecting spots thereof. The second connecting spots are embodied as joints which are a couple of pins 340 attached to the second rigid body 20 and threaded on the other side in a bearing ball or a simpler ball joint. This allows the second body 20 to be tiltable about the axis x' in relation to the mechanical constraint 39.

Figure 4:
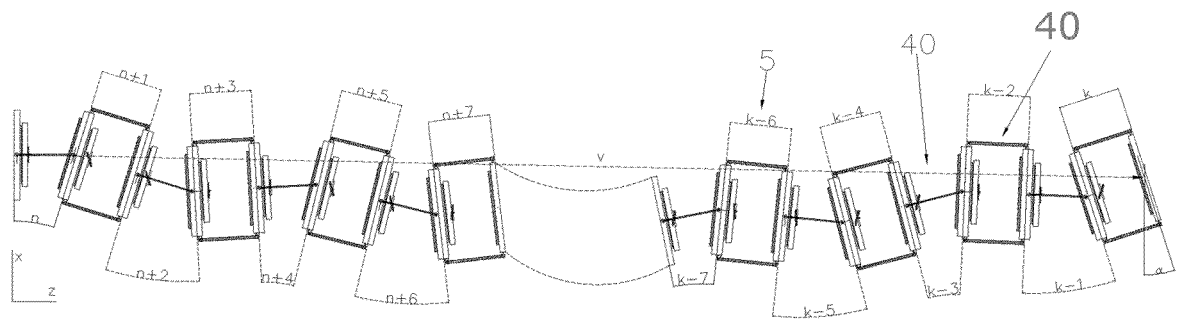
FIG. 4 shows a first embodiment of an endoscope according to the invention comprising a plurality of apparatuses of FIG. 2.

FIG. 4 shows a first embodiment of an endoscope 5 according to the invention which comprises a plurality or chain of measurement apparatuses 40. The measurement apparatuses 40 are arranged in a cascade configuration wherein alternatingly the second embodiment of the apparatus 40 described above is turned by 90°. The degrees of freedom of two consecutive rigid bodies are orthogonal each other in order to make the endoscope 5 flexible in both of the directions. Thereby, each of the second rigid bodies 20 of the $\alpha$-tiltable apparatuses forms one of the first rigid bodies 10 of the $\beta$-tiltable apparatuses 40 turned by 90°. Similarly, each of the second rigid bodies 20 of the $\beta$-tiltable apparatuses forms one of the first rigid bodies 10 of the $\alpha$-tiltable apparatuses 40 turned by 90°. In particular each rigid body 10, 20 is on one side equipped with the image sensor 150, the transparent spacer 170, the shadow mask 110 and the light source 130 and on the other side with the mirror 210. Such arrangement forms a measurement system which allows to determine the position v and the angles $\alpha$ and $\beta$ of any element k of the cascade with respect to any other element n. In particular, this can be achieved by combining the measurements and the geometrical features of the elements between k and n.

Figure 5:
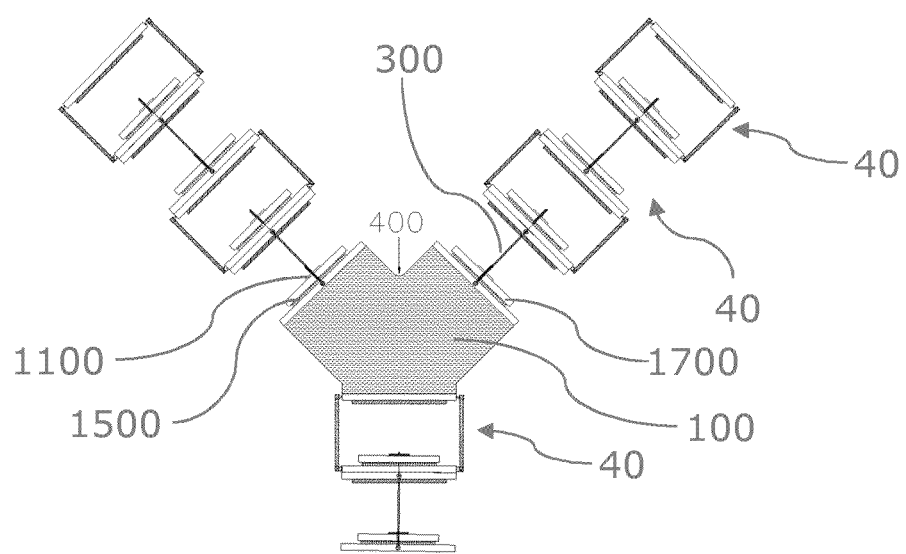
FIG. 5 shows a second embodiment of an endoscope according to the invention comprising a plurality of apparatuses of FIG. 2 and a third embodiment of an apparatus according to the invention.

In FIG. 5 a second embodiment of an endoscope according to the invention is shown. This endoscope widely embodied identical as the first endoscope 5 described above. However, one of the apparatuses is a third embodiment of an apparatus 400 according to the invention. The apparatus 400 comprises a Y-shaped base 100 forming two first rigid bodies at its two head ends and one second rigid body at its stem end. Each of the first rigid bodies of the Y-shaped base 400 is equipped with an image sensor 1500, a transparent spacer 1700, a shadow mask 1100 and a light source. The second rigid body of the Y-shaped base 400 is equipped with a mirror 2100. To each of the first and second rigid bodies of the Y-shaped base 400 chains of first apparatuses 40 are connected. Like this, branches can be formed in the endoscope which may be allow a flexible and efficient use in specific applications.

This description and the accompanying drawings that illustrate aspects and embodiments of the present invention should not be taken as limiting-the claims defining the protected invention. In other words, while the invention has been illustrated and described in detail in the drawings and foregoing description, such illustration and description are to be considered illustrative or exemplary and not restrictive. Various mechanical, compositional, structural, electrical, and operational changes may be made without departing from the spirit and scope of this description and the claims. In some instances, well-known circuits, structures and techniques have not been shown in detail in order not to obscure the invention. Thus, it will be understood that changes and modifications may be made by those of ordinary skill within the scope and spirit of the following claims. In particular, the present invention covers further embodiments with any combination of features from different embodiments described above and below. In particular, the invention can also be embodied comprising the following exemplary features:

The rigid bodies are bounded by the mechanical constraint in a way that the relative position v is fixed while both the angles α and β can change. For example, this can be implemented by the mechanical constraint comprising two lateral arms and a gimbals suspension in which the rotary joints are of the same type as disclosed before. Or in another example of this implementation, the mechanical constraint is done with one arm rigidly tied to the first rigid body and to the center of rotation c' of the second rigid body 200 through a pivot joint such as a ball joint.

The data output of the endoscope is transmitted through an electronic BUS shared among all the involved apparatuses.

The disclosure also covers all further features shown in the Figs. individually although they may not have been described in the afore or following description. Also, single alternatives of the embodiments described in the figures and the description and single alternatives of features thereof can be disclaimed from the subject matter of the invention or from disclosed subject matter. The disclosure comprises subject matter consisting of the features defined in the claims or the exemplary embodiments as well as subject matter comprising said features.

Furthermore, in the claims the word "comprising" does not exclude other elements or steps, and the indefinite article "a" or "an" does not exclude a plurality. A single unit or step may fulfil the functions of several features recited in the claims. The mere fact that certain measures are recited in mutually different dependent claims does not indicate that a combination of these measures cannot be used to advantage. The terms "essentially", "about", "approximately" and the like in connection with an attribute or a value particularly also define exactly the attribute or exactly the value, respectively. The term "about" in the context of a given numerate value or range refers to a value or range that is, e.g., within 20%, within 10%, within 5%, or within 2% of the given value or range. Components described as coupled or connected may be electrically or mechanically directly coupled, or they may be indirectly coupled via one or more intermediate components. Any reference signs in the claims should not be construed as limiting the scope.

The invention claimed is:

1. An apparatus for determining a position and orientation of a first rigid body and a second rigid body in relation to each other, comprising:
    an at least essentially punctual light source mounted stationary in relation to the first rigid body;
    an image sensor mounted stationary in relation to either the first rigid body or the second rigid body and positioned in a field of light propagated by the light source;
    a shadow mask mounted stationary in relation to either the first rigid body or the second rigid body and arranged in the field of light propagated from the light source between the light source and the image sensor;
    a computation unit configured to calculate at least one angle defining the position and orientation of the first rigid body and the second rigid body relative to each other by evaluating a shadow image generated by light propagated by the light source which passes the shadow mask and which is detected by the image sensor; and
    a mechanical constraint mounted to a first connection spot of the first rigid body and to a second connection spot of the second rigid body, wherein the mechanical constraint
        defines a fixed distance between the first connection spot of the first rigid body and the second connection spot of the second rigid body,
        is stationary in relation to one of the first rigid body or the second rigid body, and
        is variably inclinable in relation to the other one of the first rigid body or the second rigid body.

2. The apparatus according to claim 1, wherein the image sensor is mounted stationary in relation to the second rigid body.

3. The apparatus according to claim 1, wherein a mirror is mounted stationary in relation to the second rigid body and the image sensor is mounted stationary in relation to the first rigid body.

4. The apparatus according to claim 3, wherein the mirror has a curved surface.

5. The apparatus according to claim 1 further comprising a shield structure protecting the image sensor from light disturbances.

6. The apparatus according to claim 1, wherein the shadow mask is mounted stationary in relation to the first rigid body.

7. The apparatus according to claim 1, wherein the mechanical constraint is adapted to hold the first rigid body and the second rigid body in a predefined relative position to each other such that the shadow image has a one-to-one with the at least one angle.

8. The apparatus according to claim 7, wherein the relative position is fixed by the mechanical constraint such that exclusively the at least one angle is changeable.

9. The apparatus according to claim 7, wherein the computation unit is configured to calculate the one-to-one correspondence by interpolating input data provided by the image sensor in a calibration step.

10. The apparatus according to claim 1, wherein the image sensor and/or the computation unit is configured to differentiate light detected by the image sensor into light propagated by the light source and other light.

11. The apparatus according to claim 1, wherein the shadow mask comprises a pattern having distinctive elements.

12. The apparatus according to claim 1 further comprising:
    a further second rigid body;
    a further at least essentially punctual light source mounted stationary in relation to the first rigid body;
    a further image sensor mounted stationary in relation to either the first rigid body or the further second rigid body and positioned in a field of light propagated by the further light source;
    a further shadow mask mounted stationary in relation to either the first rigid body or the further second rigid body and arranged in the field of light propagated from the further light source between the further light source and the further image sensor; and a further mechanical constraint mounted to a further first connection spot of the first rigid body and to a further second connection spot of the further second rigid body, wherein the further mechanical constraint defines a fixed distance between the further first connection spot of the first rigid body and the further second connection spot of the further second rigid body, is stationary in relation to one of the first rigid body or to the further second rigid body, and is variably inclinable in relation to the other one of the first rigid body or the further second rigid body, wherein the computation unit is configured to calculate at least one further angle by evaluating a shadow image generated by light propagated from the further light source which passes the further shadow mask and which is detected by the further image sensor.

13. A method of determining a position and orientation of a first rigid body and a second rigid body in relation to each other, comprising:

mounting an at least essentially punctual light source stationary in relation to a first rigid body of the two rigid bodies;

positioning an image sensor in a field of light propagated from the light source;

mounting the image sensor stationary in relation to either the first rigid body or a second rigid body of the two rigid bodies;

mounting a shadow mask stationary in relation to either the first rigid body or the second rigid body;

arranging the shadow mask in the field of light propagated from the light source between the light source and the image sensor;

calculating at least one angle defining the position and orientation of the first rigid body and the second rigid body relative to each other by evaluating a shadow image generated by light propagated from the light source which passes the shadow mask and detected by the image sensor; and mounting a mechanical constraint to a first connection spot of the first rigid body and to a second connection spot of the second rigid body, wherein the mechanical constraint defines a fixed distance between the first connection spot of the first rigid body and the second connection spot of the second rigid body, is stationary in relation to one of the first rigid body and the second rigid body, and is variably inclinable in relation to the other one of the first rigid body and the second rigid body.

14. An endoscopic device having a longitudinal body adapted to be provided into a lumen of a human or animal body and an intervention member arranged at a distal longitudinal end region of the longitudinal body, wherein the longitudinal body comprises a series of apparatuses according to claim 1.

15. The endoscopic device according to claim 14, wherein each two consecutive rigid bodies of the series of apparatuses are rotatable orthogonal to each other.

* * * * *